(12) United States Patent
Nishimura et al.

(10) Patent No.: US 9,013,566 B2
(45) Date of Patent: Apr. 21, 2015

(54) ELECTRONIC ENDOSCOPE APPARATUS

(75) Inventors: Hisashi Nishimura, Tokyo (JP); Kaoru Kotoda, Tokyo (JP); Satoshi Tanaka, Tokyo (JP); Naruyasu Kobayashi, Kawasaki (JP); Takayuki Sato, Tokyo (JP); Kazuhiro Takizawa, Tokyo (JP); Motoo Azuma, Tokorozawa (JP)

(73) Assignee: Olympus Corporation, Tokyo (JP)

( * ) Notice: Subject to any disclaimer, the term of this patent is extended or adjusted under 35 U.S.C. 154(b) by 374 days.

(21) Appl. No.: 13/528,385

(22) Filed: Jun. 20, 2012

(65) Prior Publication Data

US 2012/0320177 A1 Dec. 20, 2012

(30) Foreign Application Priority Data

Jun. 20, 2011 (JP) ................................. 2011-136411

(51) Int. Cl.
*A61B 1/04* (2006.01)
*A61B 1/00* (2006.01)

(52) U.S. Cl.
CPC .............. *A61B 1/04* (2013.01); *A61B 1/00006* (2013.01)

(58) Field of Classification Search
CPC ....................................................... A61B 1/04
USPC ............................................................ 348/65
See application file for complete search history.

(56) References Cited

U.S. PATENT DOCUMENTS

2009/0027490 A1* 1/2009 Hirai et al. ...................... 348/65
2009/0102917 A1* 4/2009 Minakuchi ...................... 348/65

FOREIGN PATENT DOCUMENTS

JP 2001-275956 A 10/2001

* cited by examiner

*Primary Examiner* — Dave Czekaj
*Assistant Examiner* — Berteau Joisil
(74) *Attorney, Agent, or Firm* — Westerman, Hattori, Daniels & Adrian, LLP

(57) ABSTRACT

A phase comparing unit compares a phase of an imaging-side synchronization signal with a phase of a display-side clock, and controls oscillation of a display-side clock generating unit based on a result of the comparison. A display timing adjusting unit receives a video signal output from an endoscope at a timing based on the imaging-side synchronization signal and adjusts a synchronization timing of the received video signal to a synchronization timing based on a display-side synchronization signal.

10 Claims, 10 Drawing Sheets

ELECTRONIC ENDOSCOPE APPARATUS

BACKGROUND OF THE INVENTION

1. Field of the Invention

The present invention relates to an electronic endoscopic apparatus that includes an endoscope on which an imaging unit is mounted and an image processor performing predetermined image processing on a video signal from the endoscope.

Priority is claimed on Japanese Patent Application No. 2011-136411 filed on Jun. 20, 2011, the contents of which are incorporated herein by reference.

2. Description of Related Art

In recent years, the number of pixels of solid-state imaging devices, such as a CCD (Charge Coupled Device) and a CMOS (Complementary Metal Oxide Semiconductor) sensor, has increased with the advance of semiconductor technology. This tendency is not an exception even in electronic endoscope apparatuses, and the number of pixels of solid-state imaging devices included in the electronic endoscope apparatuses is increasing.

With an increase in the number of pixels of the solid-state imaging devices, the frequency of a clock signal that is required for image processing has also become higher, and causing various problems as a result. For example, in the structure of an electronic endoscope apparatus, the distal end portion of a scope on which a solid-state imaging device is mounted, and an image processor that performs image processing are separated, and signal degradation on a transmission path between the solid-state imaging device and the image processor has a tendency to occur. Additionally, if the frequency of the signal becomes high, the influence of signal degradation on the transmission path between the solid-state imaging device and the image processor becomes greater still. Additionally, leakage of electromagnetic waves caused by high frequency signals flowing through the transmission path between the solid-state imaging device and the image processor also becomes more significant.

An electronic endoscopic apparatus is proposed in Japanese Unexamined Patent Application Publication No. 2001-275956. In this electronic endoscopic apparatus, a waveform smoothing circuit is inserted into an output portion of an electronic scope. Due to this waveform smoothing circuit, high-frequency noise released between the electronic scope and a processor device is inhibited.

Japanese Unexamined Patent Application Publication No. 2001-275956 contains no teaching in terms of synchronization between an endoscope and a monitor instrument. Since a solid-state imaging device having various angles of view depending on a target to be observed and use is mounted on the endoscope, an operating frequency and an angle of view are different according to the endoscope. Accordingly, to display an image captured by the endoscope on the monitor, frequency conversion adapted to a synchronization signal of the monitor is required.

Depending on a relation between a display clock and an imaging clock, there is a subtle difference between a cycle in which the endoscope captures an image of one frame and a cycle in which the monitor instrument displays an image of one frame. As such, the two cycles are gradually shifted in phase. Further, when the phase shift between the two cycles exceeds a time of one frame, a phenomenon called "passing" or "frame dropping" takes place.

FIG. 10 schematically shows a relation between a one-frame cycle based on an imaging clock and a one-frame cycle based on a display clock. As shown in FIG. 10, the one-frame cycle based on the imaging clock and the one-frame cycle based on the display clock are subtly different from each other, and a shift of the one-frame cycle (D0, D1, D2) increases with the lapse of time.

SUMMARY OF THE INVENTION

According to a first aspect of the present invention, an electronic endoscopic apparatus includes an endoscope and an image processor. The endoscope includes an imaging unit that converts optical information into an electric signal based on a scope-side clock and a scope-side synchronization signal and output the converted electric signal as a video signal; a first multiplying/dividing unit that multiplies and/or divide a transmission clock transmitted from the image processor to generate the scope-side clock; and a scope-side synchronization signal generating unit that generates the scope-side synchronization signal. The image processor includes an imaging-side clock generating unit that generates an imaging-side clock; a second multiplying/dividing unit that multiplies and/or divide the imaging-side clock to generate the transmission clock; a display-side clock generating unit that generates a display-side clock; an imaging-side synchronization signal generating unit that generates an imaging-side synchronization signal in the image processor; an display-side synchronization signal generating unit that generates an display-side synchronization signal in the image processor based on the display-side clock; a phase comparing unit that compares a phase of the imaging-side synchronization signal with a phase of the display-side clock and control an oscillation of the display-side clock generating unit based on a result of the comparison; and a display timing adjusting unit that receives the video signal output from the endoscope at a timing based on the imaging-side synchronization signal and adjust a synchronization timing of the received video signal to a synchronization timing based on the display-side synchronization signal. A frequency of the display-side clock is M/N times a frequency of the imaging-side clock (where M and N are arbitrary natural numbers).

According to a second aspect of the present invention, in the electronic endoscopic apparatus, in the endoscope, the scope-side synchronization signal generating unit generates the scope-side synchronization signal synchronized with the imaging-side synchronization signal based on the scope-side clock and the imaging-side synchronization signal. In the image processor, the imaging-side synchronization signal generating unit spontaneously generates the imaging-side synchronization signal based on the imaging-side clock and transmits the generated signal to the phase comparing unit and the scope-side synchronization signal generating unit.

According to a third aspect of the present invention, in the electronic endoscopic apparatus, in the endoscope, the scope-side synchronization signal generating unit spontaneously generates the scope-side synchronization signal based on the scope-side clock. In the endoscope, the imaging-side synchronization signal generating unit includes a synchronization signal generating circuit that spontaneously generates a first imaging-side synchronization signal in the image processor based on the imaging-side clock; and a receiving unit that receives the scope-side synchronization signal output from the endoscope and output the received signal as a second imaging-side synchronization signal in the image processor. The phase comparing unit compares a phase of the first imaging-side synchronization signal with the phase of the display-side clock and controls the oscillation of the display-side clock generating unit based on a result of the comparison. The display timing adjusting unit has a synchronization frame memory, writes the video signal output from the endoscope to the synchronization frame memory at a timing based on the second imaging-side synchronization signal, and reads out the video signal from the synchronization frame memory at a timing based on the scope-side synchronization signal.

According to a fourth aspect of the present invention, in the electronic endoscopic apparatus, in the endoscope, the scope-side synchronization signal generating unit spontaneously generates the scope-side synchronization signal based on the scope-side clock. In image processor, the imaging-side synchronization signal generating unit has a receiving unit that receives the scope-side synchronization signal output from the endoscope and outputs the received signal as the imaging-side synchronization signal.

According to a fifth aspect of the present invention, in the electronic endoscopic apparatus, the endoscope includes an electro-optic conversion unit that converts the video signal into an optical signal. The image processor includes a photoelectric conversion unit that converts the optical signal into the video signal.

According to a sixth aspect of the present invention, in the electronic endoscopic apparatus, the endoscope includes a conversion unit that converts the video signal into a differential signal. The image processor includes a demodulating unit that demodulates the differential signal into the video signal.

According to a seventh aspect of the present invention, in the electronic endoscopic apparatus, the endoscope includes a radio transmitting unit that wirelessly transmits the video signal. The image processor includes a radio receiving unit that receives the video signal that is wirelessly transmitted by the radio transmitting unit.

According to an eighth aspect of the present invention, in the electronic endoscopic apparatus, the endoscope includes a compressing unit that compresses the video signal. The image processor includes an expansion unit that expands the video signal compressed by the compressing unit.

According to a ninth aspect of the present invention, in the electronic endoscopic apparatus, the endoscope includes a superimposing unit that superimposes the scope-side synchronization signal on the video signal. The image processor includes a separating unit that separates the scope-side synchronization signal from the video signal on which the scope-side synchronization signal is superimposed by the superimposing unit, and output the separated signal to the receiving unit as the second imaging-side synchronization signal.

According to a tenth aspect of the present invention, in the electronic endoscopic apparatus, the endoscope includes a superimposing unit that superimposes the scope-side synchronization signal on the video signal. The image processor includes a separating unit that separates the scope-side synchronization signal from the video signal on which the scope-side synchronization signal is superimposed by the superimposing unit, and output the separated signal to the receiving unit as the imaging-side synchronization signal.

DETAILED DESCRIPTION OF THE INVENTION

Hereinafter, embodiments of the present invention will be described with reference to the drawings.
(First Embodiment)

Figure 1:
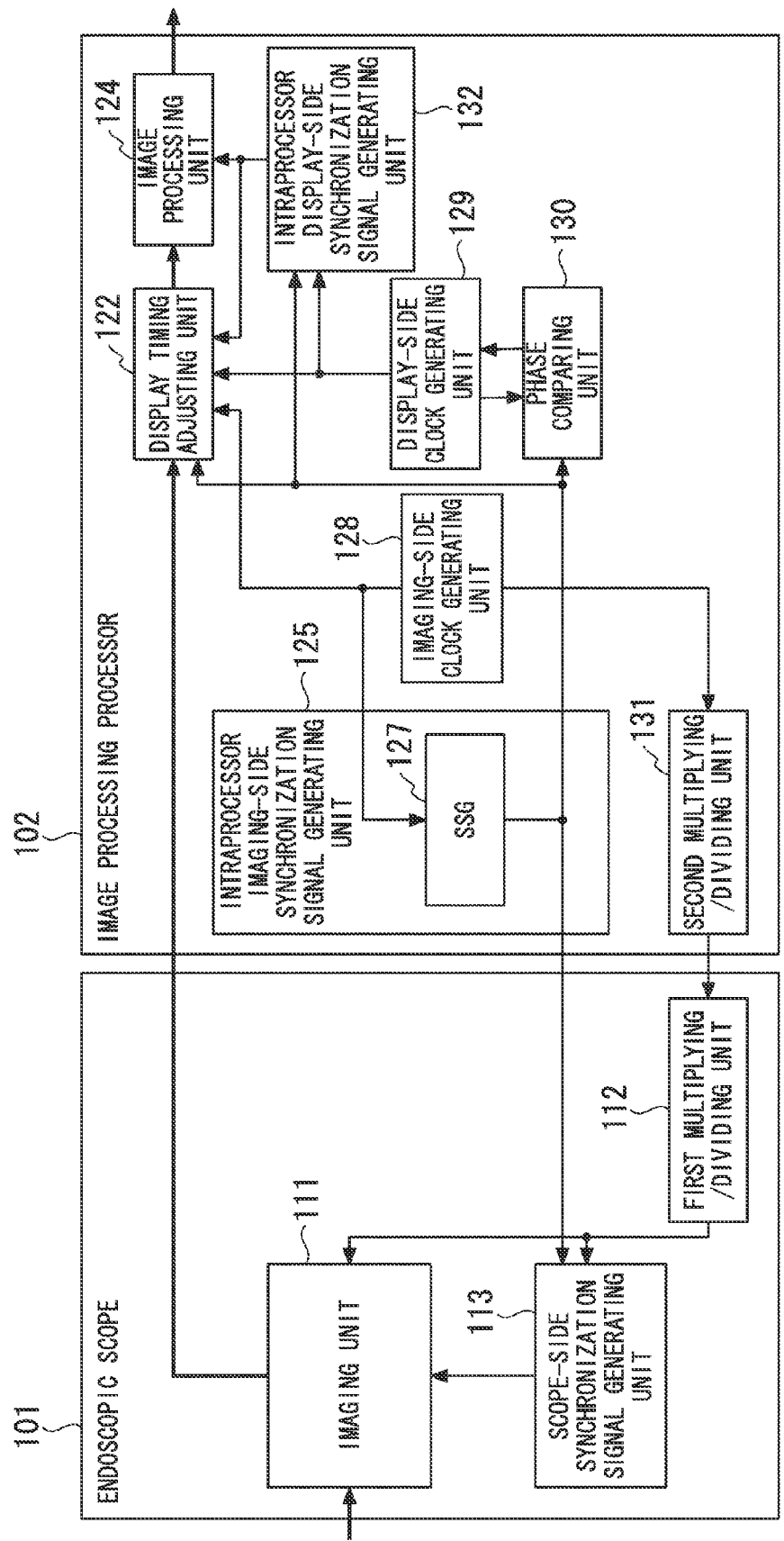
FIG. 1 is a block diagram showing a configuration of an electronic endoscopic apparatus according to a first embodiment of the present invention.

First, a first embodiment of the present invention will be described. FIG. 1 shows a configuration of an electronic endoscopic apparatus according to the present embodiment. As shown in FIG. 1, the electronic endoscopic apparatus includes an endoscope 101 and an image processor 102. The endoscope 101 includes an imaging unit 111, a first multiplying/dividing unit 112, and a scope-side synchronization signal generating unit 113. The image processor 102 includes a display timing adjusting unit 122, an image processing unit 124, an imaging-side synchronization signal generating unit 125, an imaging-side clock generating unit 128, a display-side clock generating unit 129, a phase comparing unit 130, a second multiplying/dividing unit 131, and a display-side synchronization signal generating unit 132.

In the endoscope 101, the imaging unit 111 is of a charge-coupled device (CCD) or complementary metal oxide semiconductor (CMOS) sensor that converts optical information into an electric signal and outputs the converted electric signal as a video signal to the image processor 102. The first multiplying/dividing unit 112 appropriately performs only multiplication or a combination of the multiplication and the division on a transmission clock transmitted from the image processor 102, and generates a scope-side clock which includes a higher frequency than the transmission clock. The scope-side synchronization signal generating unit 113 generates a scope-side synchronization signal required to drive the imaging unit 111 on the basis of the scope-side clock.

This scope-side synchronization signal is a synchronization signal that is synchronized to the imaging-side synchronization signal transmitted from the image processor 102 and that has the same cycle as the imaging-side synchronization signal. When a CMOS sensor is used for the imaging unit 111, the imaging unit 111, the first multiplying/dividing unit 112, and the scope-side synchronization signal generating unit 113 can be mounted on the same chip.

In the image processor 102, as a configuration for generating a clock, the imaging-side clock generating unit 128 and the display-side clock generating unit 129 are independently provided. The imaging-side clock generating unit 128 generates an imaging-side clock, while the display-side clock generating unit 129 generates a display-side clock.

The second multiplying/dividing unit 131 appropriately performs only division or a combination of the multiplication and the division on the imaging-side clock, and generates a transmission clock which includes a lower frequency than that required to drive the imaging unit 111. The transmission clock output from the second multiplying/dividing unit 131 is transmitted to the endoscope 101.

Recently, the number of pixels of a solid-state imaging device is increasing, and a frequency required to drive the solid-state imaging device is rising.

It is difficult to transmit a high-frequency clock through a long scope cable of an endoscope, and occurrence of undesired radiation becomes a problem. As such, it is important to suppress the frequency of the transmission clock to a low frequency. As described above, the transmission clock transmitted to the endoscope 101 is converted into the scope-side clock, which has a frequency required to drive the imaging unit 111, by the first multiplying/dividing unit 112.

The imaging-side synchronization signal generating unit 125 includes a synchronization signal generator (SSG) 127 that spontaneously generates an imaging-side synchronization signal on the basis of the imaging-side clock. To spontaneously generate the imaging-side synchronization signal is defined as generating the imaging-side synchronization signal independently of other synchronization signals without reference to the other synchronization signals. The imaging-side synchronization signal generated by the imaging-side synchronization signal generating unit 125 is transmitted to the endoscope 101 as an imaging-side synchronization signal, is supplied to the scope-side synchronization signal generating unit 113 as well as the display timing adjusting unit 122, the phase comparing unit 130, and the display-side synchronization signal generating unit 132, and is used as a signal indicating a frame start position of the video signal.

On the basis of the imaging-side synchronization signal, the phase comparing unit 130 makes a phase comparison with the display-side clock generated by the display-side clock generating unit 129, and as a result of the comparison, outputs a control signal to the display-side clock generating unit 129 to control the display-side clock in the display-side clock generating unit 129. On the basis of the control signal from the phase comparing unit 130, the display-side clock generating unit 129 controls a frequency of the display-side clock so as to match a phase of the imaging-side synchronization signal and a phase of the display-side clock. Thereby, a synchronization relation between the imaging-side clock and the display-side clock is secured such that a cycle of an imaging-side vertical synchronization signal (one of the imaging-side synchronization signals) and a cycle of a display-side vertical synchronization signal (one of the display-side synchronization signals) are completely identical to each other.

Figure 2:
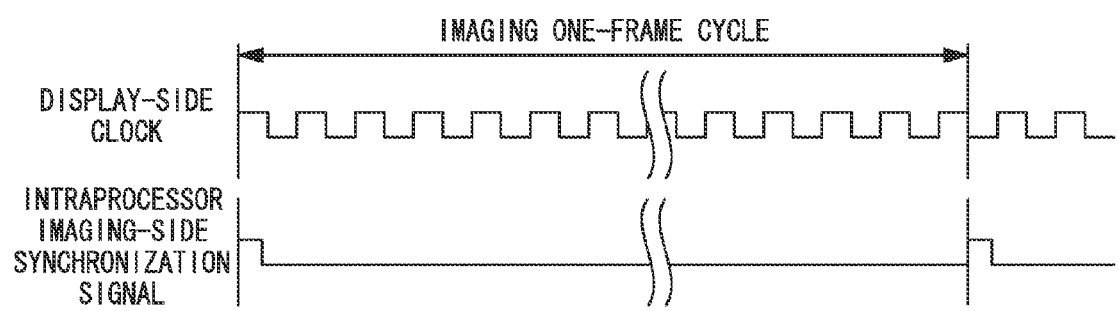
FIG. 2 is a timing chart that explains an operation of a phase comparing unit mounted in the electronic endoscopic apparatus according to the first embodiment of the present invention.

FIG. 2 shows operations of the phase comparing unit 130. The phase comparing unit 130 compares, for instance, a position of a rising edge of the display-side clock and a position of a rising edge of the imaging-side synchronization signal (imaging-side vertical synchronization signal in an example of FIG. 2). On the basis of a difference between the two edge positions, the phase comparing unit 130 outputs a control signal to the display-side clock generating unit 129. On the basis of the control signal, the display-side clock generating unit 129 controls an oscillation state of the display-side clock, i.e., a frequency of the display-side clock. Thereby, the rising edge position of the display-side clock is identical to the rising edge position of the imaging-side synchronization signal. Thus, it is possible to secure the synchronization between the display-side clock and the imaging-side clock. In FIG. 2, the example in which the imaging-side vertical synchronization signal is used when the phase thereof is compared with the phase of the display-side clock is shown. However, an imaging-side horizontal synchronization signal may be used.

The frequency of the display-side clock is defined as 74.1758 MHz according to the standards in the case of a high definition television (HDTV). When a frequency of an imaging clock is selected, the frequency of the display-side clock becomes a frequency corresponding to a value obtained by multiplying (times N, N: natural number) or dividing (times 1/M, M: natural number) the frequency of the imaging clock by the natural number, and similarly, a frequency obtained by multiplying a frequency of the display-side vertical synchronization signal which is defined as 59.94 Hz according to the standards of the HDTV by a natural number is selected as the frequency of the display-side clock. Thereby, even when the frequency of the display-side clock is minutely adjusted based on the imaging clock, the frequency of the display-side clock can be fixed so as to be within an allowable range of a frequency at which a monitor can be serviced, and stabilized display can be realized.

The display timing adjusting unit 122 receives the video signal transmitted from the endoscope 101 using the imaging-side clock that is fed from imaging-side clock generating unit 128 and the imaging-side synchronization signal that is generated by the imaging-side synchronization signal generating unit 125. Further, the display timing adjusting unit 122 converts the received video signal into a video signal synchronized to a timing of the display-side synchronization signal generated by the display-side synchronization signal generating unit 132 using the frequency of the display-side clock generated by the display-side clock generating unit 129, and feeds the converted video signal to the image processing unit 124. In this case, the imaging-side synchronization signal and the display-side synchronization signal are used as a signal indicating a frame start timing of the video signal.

With the configuration as described above, the display timing adjusting unit 122 adjusts a synchronization timing of the video signal based on the imaging-side synchronization signal to a synchronization timing based on the display-side synchronization signal. That is, the display timing adjusting unit 122 is allowed to adjust a one-frame cycle of the video signal from an imaging-side cycle based on the imaging-side synchronization signal to a display-side cycle based on the display-side synchronization signal.

The display-side synchronization signal generating unit 132 generates a display-side synchronization signal in the image processor so as to maintain a certain phase relation with the imaging-side synchronization signal using the display-side clock and the imaging-side synchronization signal. The display-side synchronization signal generated by the display-side synchronization signal generating unit 132 is output to the display timing adjusting unit 122 and the image processing unit 124, and is used as a signal indicating the frame start timing of the video signal. Since the display-side synchronization signal is generated from the display-side clock, which is adjusted to be synchronized with the imaging-side clock, by making adjustment so as to be synchronized with the imaging-side synchronization signal, a length of a one-frame cycle of the imaging-side synchronization signal can be identical to a length of a one-frame cycle of the display-side synchronization signal.

The video signal output by the imaging unit 111 is synchronized to the scope-side synchronization signal. The scope-side synchronization signal and the display-side synchronization signal are configured so as to maintain a certain phase relation via the imaging-side synchronization signal. Accordingly, the display timing adjusting unit 122 suffices only to replace the video signal from the scope-side clock to the display-side clock to adjust a timing using a line memory. More particularly, the display timing adjusting unit 122 may receive the video signal transmitted from the endoscope 101 to write to the line memory using the imaging-side clock and the imaging-side synchronization signal, read out the video signal from the line memory using the display-side clock and the display-side synchronization signal, and feed the read video signal to the image processing unit 124.

As will be described in the second embodiment, if the display timing adjusting unit 122 has a synchronization frame memory, the display-side synchronization signal generating unit 132 may generate an display-side synchronization signal of which cycle is merely coincident with that of the imaging-side synchronization signal without reference to the imaging-side synchronization signal.

The image processing unit 124 is an image processing circuit that conducts gamma ( ) correction, color conversion, edge enhancement, and the like. The image processing unit 124 operates based on the display-side clock and the display-side synchronization signal, and conducts the image processing on the video signal. Then, the video signal is output to a monitor, which is not shown.

As described above, according to the present embodiment, the phase comparing unit 130 compares the phase of the imaging-side synchronization signal with the phase of the display-side clock, and controls the oscillation of the display-side clock generating unit 129 on the basis of a result of the comparison. Thereby, it is possible to synchronize the imaging-side synchronization signal and the display-side clock with each other. Further, the display timing adjusting unit 122 receives the video signal output from the endoscope 101 at a timing based on the imaging-side synchronization signal, and adjusts the synchronization timing of the received video signal to the synchronization timing based on the display-side synchronization signal generated on the basis of the display-side clock. Thereby, the one-frame cycle of the video signal can be adjusted to the cycle based on the display-side synchronization signal from the cycle based on the imaging-side synchronization signal. Furthermore, since the display-side synchronization signal is generated from the display-side clock adjusted so as to be synchronized with the imaging-side clock, the length of the one-frame cycle of the imaging-side synchronization signal can be identical to the length of the one-frame cycle of the display-side synchronization signal. According to the foregoing, the synchronization between the imaging and the displaying is secured, and "passing" or "frame dropping" can be prevented.

Further, since no clock generating unit is required for the endoscope 101, the endoscope can be simplified.

Since the imaging-side clock generating unit 128 and the display-side clock generating unit 129 are independent from each other, the frequency of the imaging-side clock can be selected in response to a variety of endoscopes 101.

Further, even when the scope is modified, the display-side clock can be stabilized and generated.

Further, the frequency that is M/N times the frequency of the imaging-side clock (where M and N are arbitrary natural numbers) is selected as the frequency of the display-side clock, and the frequency of the display-side clock is minutely adjusted within an allowable range. Thereby, the cycle of the scope-side imaging synchronization signal generated from the scope-side clock based on the imaging-side clock can be completely identical to the cycle of the display-side synchronization signal generated from the display-side clock, and "passing" or "frame dropping" can be prevented.

The simple multiplication and division based on the imaging-side clock are conducted to generate the transmission clock transmitted to the endoscope 101, and the frequency of the transmission clock is suppressed so as to be lower than the frequency required to drive the imaging unit 111. Thereby, the problem with signal degradation and occurrence of electromagnetic noise can be reduced. Further, in the endoscope 101, a simple multiplying circuit and a simple dividing circuit are used, and the scope-side clock of the frequency required to drive the imaging unit 111 can be generated.

In addition, the imaging-side synchronization signal is transmitted from the image processor 102 to the endoscope 101, and the imaging unit 111 is driven on the basis of the transmitted signal. Thereby, even when the memory for synchronization provided to the display timing adjusting unit 122 has a low capacity, "passing" or "frame dropping" can be prevented.

(Second Embodiment)

Figure 3:
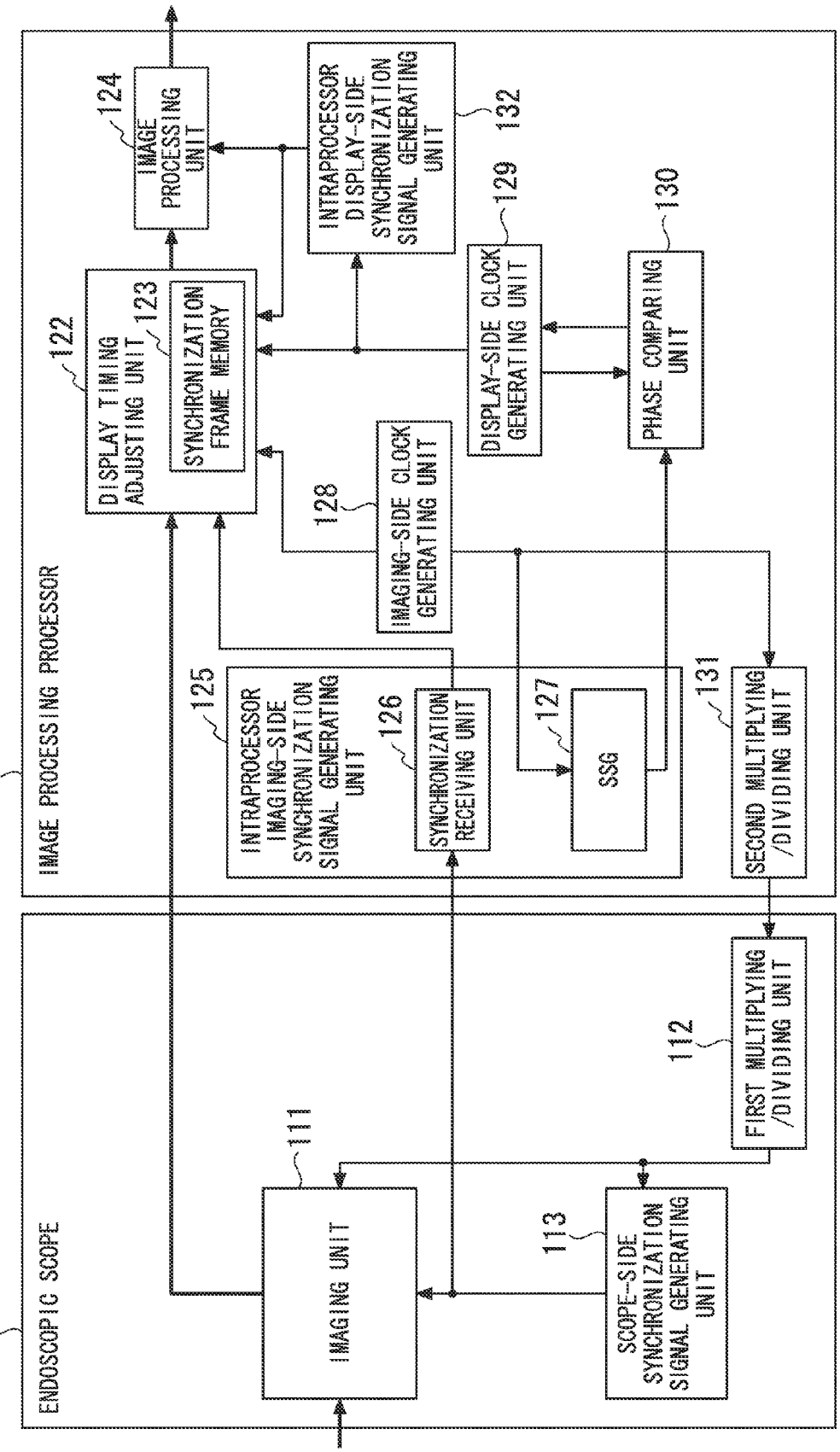
FIG. 3 is a block diagram showing a configuration of an electronic endoscopic apparatus according to a second embodiment of the present invention.

Next, a second embodiment of the present invention will be described. FIG. 3 shows a configuration of an electronic endoscopic apparatus according to the present embodiment. Hereinafter, portions different from those of the first embodiment will be described.

In an endoscope 101, a scope-side synchronization signal generating unit 113 spontaneously generates a scope-side synchronization signal on the basis of a scope-side clock output from a first multiplying/dividing unit 112. Spontaneously generating the scope-side synchronization signal is defined as generating the scope-side synchronization signal independently of other synchronization signals without reference to the other synchronization signals. The scope-side synchronization signal generated by the scope-side synchronization signal generating unit 113 is output to an imaging unit 111, and is simultaneously transmitted to an image processor 102.

In the image processor 102, an imaging-side synchronization signal generated by the synchronization signal generator 127 inside of an imaging-side synchronization signal generating unit output 125 is output to a phase comparing unit 130 as a first imaging-side synchronization signal in the image processor. An operation of the phase comparing unit 130 is similar to that described in the first embodiment, because a signal used for phase comparison is only changed from the imaging-side synchronization signal in the first embodiment to the first imaging-side synchronization signal.

The imaging-side synchronization signal generating unit 125 has a synchronization receiving unit 126 that receives the scope-side synchronization signal output from the endoscope 101 and outputs the received signal to a display timing adjusting unit 122 as a second imaging-side synchronization signal in the image processor for display timing adjustment.

The display timing adjusting unit 122 has a synchronization frame memory 123. The display timing adjusting unit 122 receives a video signal transmitted from the endoscope 101 to write to the synchronization frame memory 123 using an imaging-side clock fed from an imaging-side clock generating unit 128 and the imaging-side synchronization signal generated by the imaging-side synchronization signal generating unit 125. Further, the display timing adjusting unit 122 reads out the video signal from the synchronization frame memory 123 using a display-side clock generated by a display-side clock generating unit 129 and an display-side synchronization signal in the image processor generated by an display-side synchronization signal generating unit 132, and feeds the read video signal to an image processing unit 124. In this case, the second imaging-side synchronization signal and the display-side synchronization signal are used as a signal indicating a frame start timing of the video signal.

With the configuration as described above, the display timing adjusting unit 122 adjusts a synchronization timing of the video signal based on the imaging-side synchronization signal to a synchronization timing based on the display-side synchronization signal. That is, the display timing adjusting unit 122 is allowed to adjust a one-frame cycle of the video signal from an imaging-side cycle based on the imaging-side synchronization signal to a display-side cycle based on the display-side synchronization signal.

As described above, according to the present embodiment, the transmission of the synchronization signal from the image processor 102 to the endoscope 101 become unnecessary. Further, since the scope-side synchronization signal generating unit 113 spontaneously generates the scope-side synchronization signal, a drive timing of the imaging unit 111 can be freely determined on the side of the endoscope 101. Even after launching of the image processor 102, a new endoscope in which "passing" or "frame dropping" does not take place can be relatively easily added.

(Third Embodiment)

Figure 4:
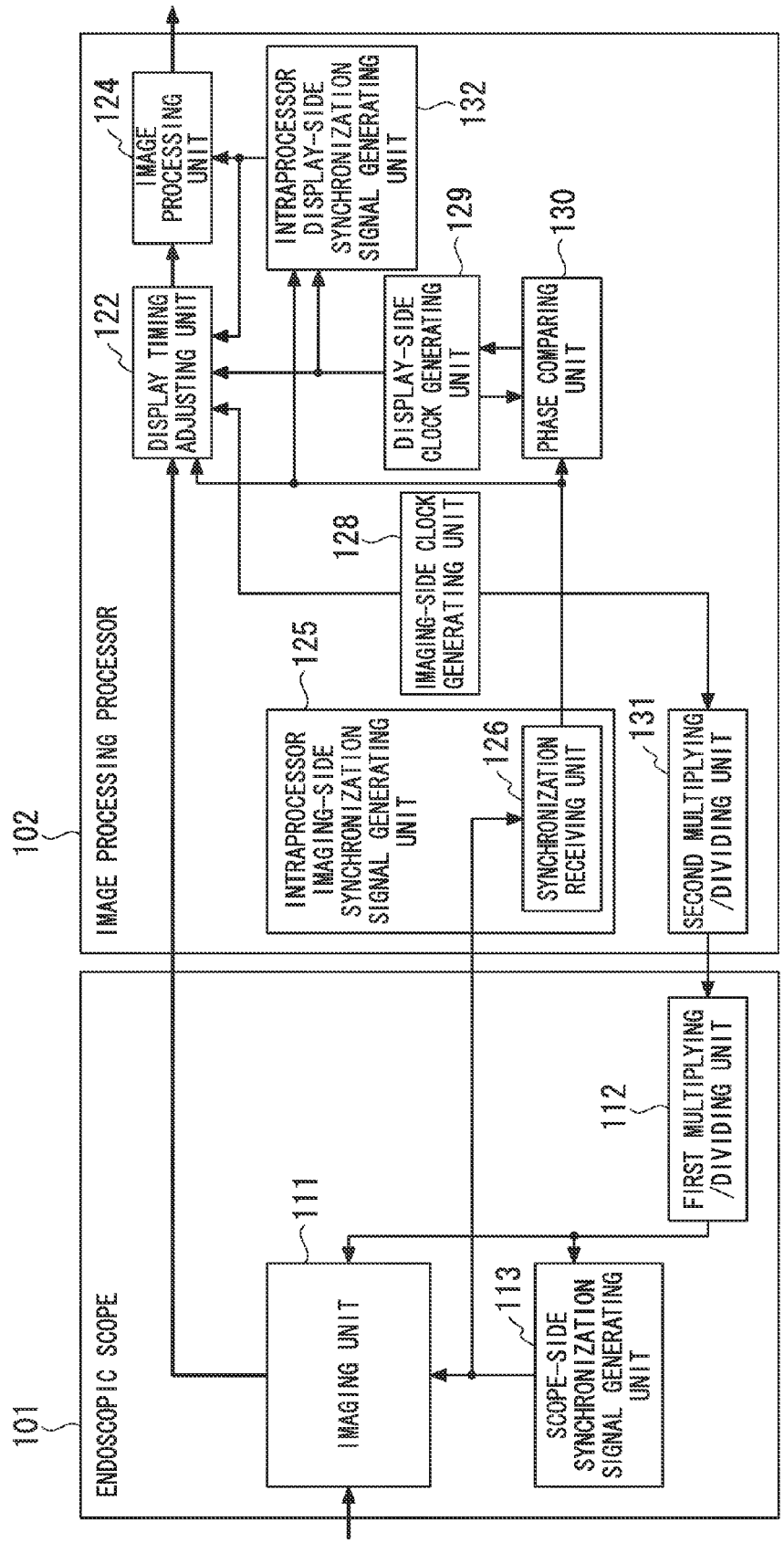
FIG. 4 is a block diagram showing a configuration of an electronic endoscopic apparatus according to a third embodiment of the present invention.

Next, a third embodiment of the present invention will be described. FIG. 4 shows a configuration of an electronic endoscopic apparatus according to the present embodiment. Hereinafter, portions different from those of the first and second embodiments will be described.

An imaging-side synchronization signal generating unit 125 of the present embodiment is equipped with a synchronization receiving unit 126 without the synchronization signal generator 127. The synchronization receiving unit 126 receives a scope-side synchronization signal output from an endoscope 101, and outputs the received signal to a display timing adjusting unit 122, a phase comparing unit 130, and an display-side synchronization signal generating unit 132 as an imaging-side synchronization signal in the image processor. Operations of the display timing adjusting unit 122, the phase comparing unit 130, and the display-side synchronization signal generating unit 132 are similar to those described in the first embodiment.

As described above, according to the present embodiment, no synchronization signal needs to be transmitted from an image processor 102 to the endoscope 101. Further, since a scope-side synchronization signal generating unit 113 spontaneously generates a scope-side synchronization signal, a drive timing of the imaging unit 111 can be freely determined on the side of the endoscope 101. Even after launching of the image processor 102, a new endoscope in which "passing" or "frame dropping" does not take place can be relatively easily added.

Further, the display-side synchronization signal has the same cycle as the imaging-side synchronization signal, and maintains a certain phase relation to be synchronized with the imaging-side synchronization signal. As such, a delay time from imaging to displaying is always kept constant, and occurrence of "passing" or "frame dropping" can be prevented.

(Fourth Embodiment)

Figure 5:
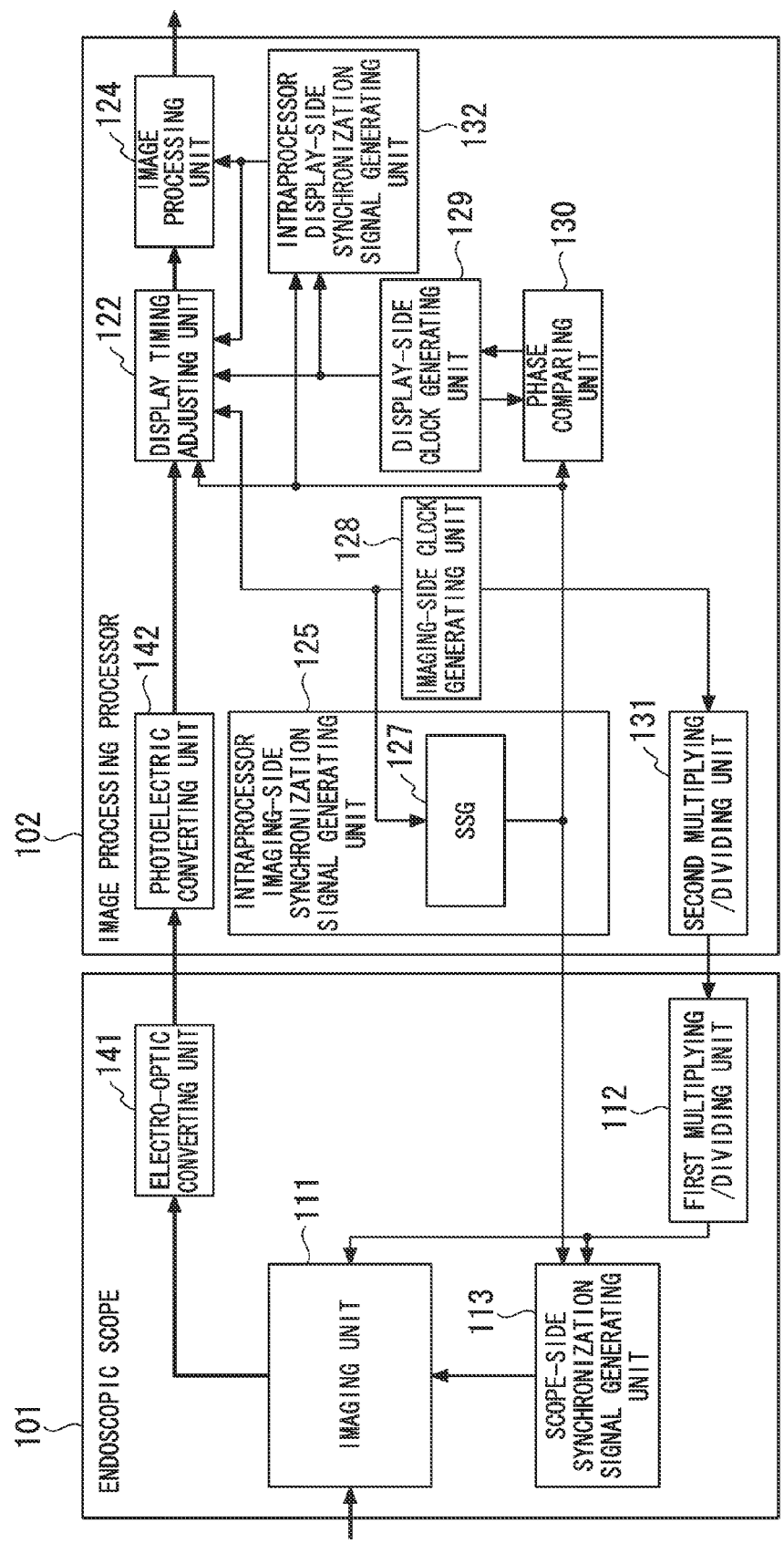
FIG. 5 is a block diagram showing a configuration of an electronic endoscopic apparatus according to a fourth embodiment of the present invention.

Next, a fourth embodiment of the present invention will be described. FIG. 5 shows a configuration of an electronic endoscopic apparatus according to the present embodiment. Hereinafter, portions different from those of the first embodiment will be described.

An endoscope 101 is equipped with an electro-optic conversion unit 141 at an output last-stage of a video signal. The electro-optic conversion unit 141 converts the video signal output from an imaging unit 111 into an optical signal, and transmits the converted signal to an image processor 102. The image processor 102 is equipped with a photoelectric conversion unit 142 at an input first-stage of the video signal. The photoelectric conversion unit 142 receives the optical signal transmitted from the endoscope 101, and returns the received optical signal back to the electrical video signal. In this way, in the present embodiment, the video signal is transmitted between the endoscope 101 and the image processor 102 using the optical signal.

In the second or third embodiment, as in the present embodiment, the electronic endoscopic apparatus may be configured so that the video signal is transmitted between the endoscope 101 and the image processor 102 using the optical signal.

As described above, according to the present embodiment, the video signal is transmitted using the optical signal. Thereby, it is possible to expect improvement in resistance to noise disturbance and reduction in magnetic noise. Further, an insulating process for securing safety of a test subjects becomes easy.

(Fifth Embodiment)

Figure 6:
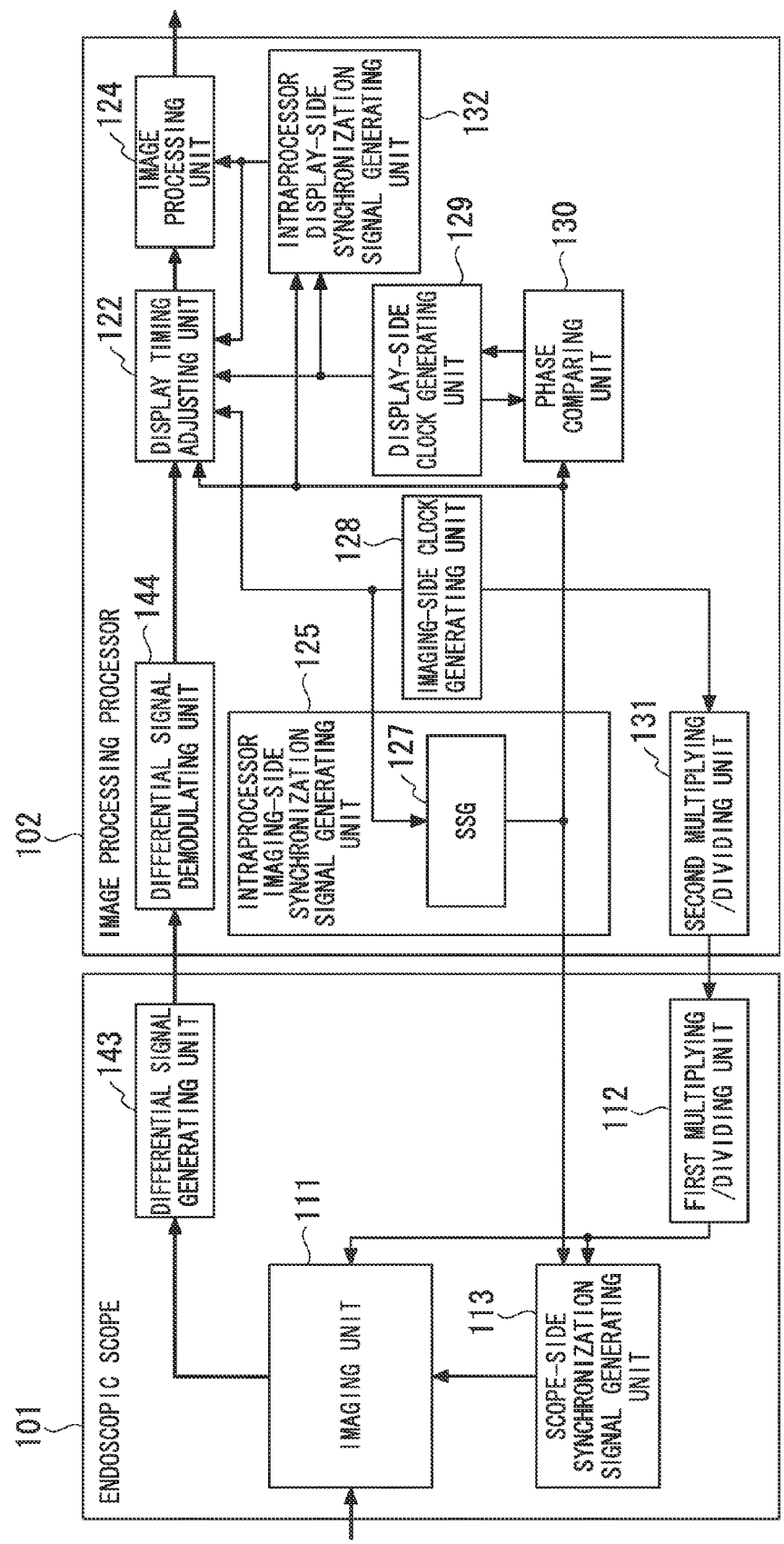
FIG. 6 is a block diagram showing a configuration of an electronic endoscopic apparatus according to a fifth embodiment of the present invention.

Next, a fifth embodiment of the present invention will be described. FIG. 6 shows a configuration of an electronic endoscopic apparatus according to the present embodiment. Hereinafter, portions different from those of the first embodiment will be described.

An endoscope 101 is equipped with a differential signal generating unit 143 at an output last-stage of a video signal. The differential signal generating unit 143 converts the video signal output from an imaging unit 111 into a differential signal, and transmits the converted signal to an image processor 102. The image processor 102 is equipped with a differential signal demodulating unit 144 at an input first-stage of the video signal. The differential signal demodulating unit 144 receives the differential signal transmitted from the endoscope 101, and demodulates the received differential signal into the original video signal. In this way, in the present embodiment, the video signal is transmitted between the endoscope 101 and the image processor 102 using the differential signal.

In the second or third embodiment, as in the present embodiment, the electronic endoscopic apparatus may be configured so that the video signal is transmitted between the endoscope 101 and the image processor 102 using the differential signal.

As described above, according to the present embodiment, the differential signal is used to transmit the video signal. Thereby, it is possible to increase resistance to noise disturbance.

(Sixth Embodiment)

Figure 7:
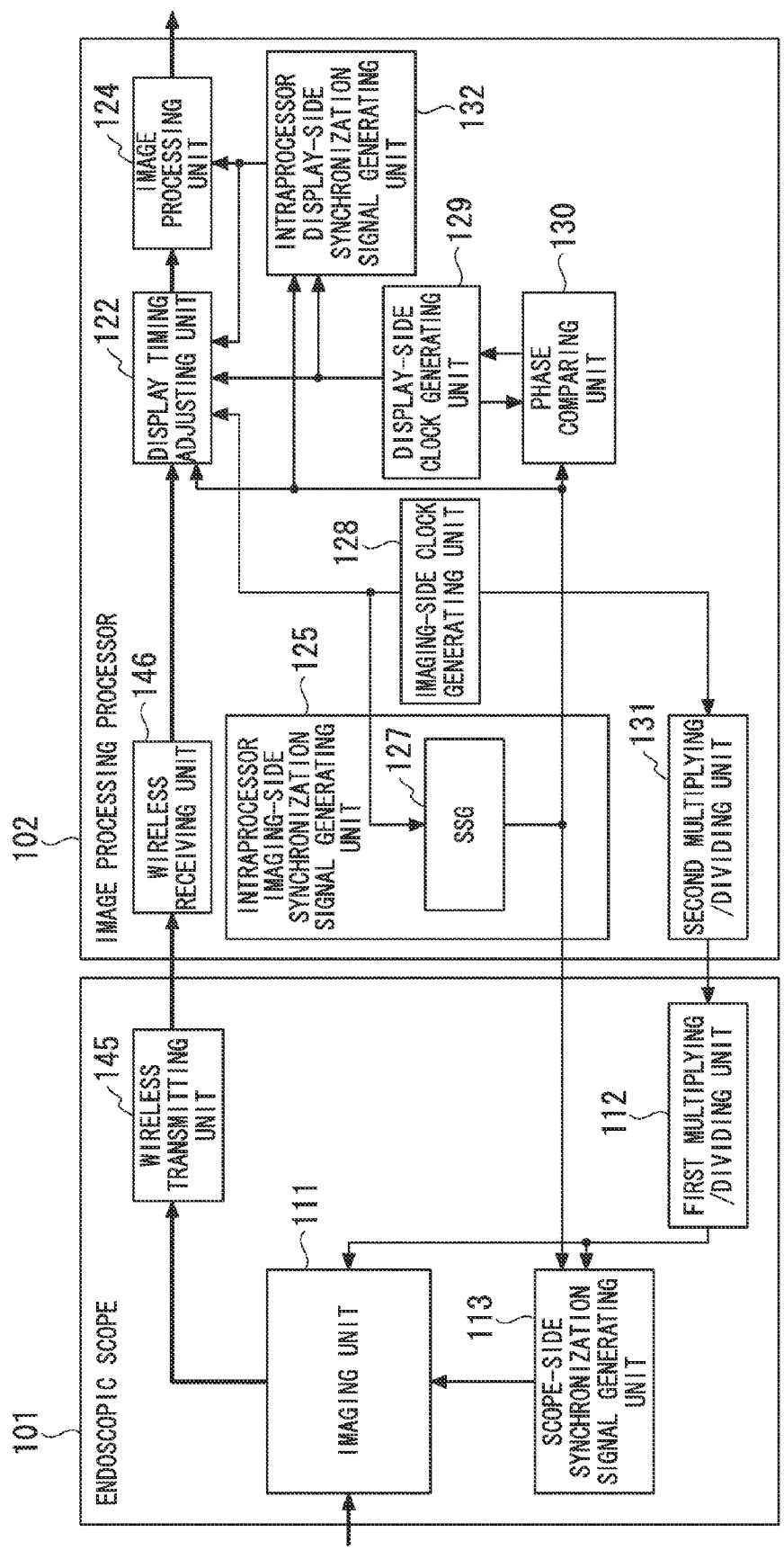
FIG. 7 is a block diagram showing a configuration of an electronic endoscopic apparatus according to a sixth embodiment of the present invention.

Next, a sixth embodiment of the present invention will be described. FIG. 7 shows a configuration of an electronic endoscopic apparatus according to the present embodiment. Hereinafter, portions different from those of the first embodiment will be described.

An endoscope 101 is equipped with a radio transmitting unit 145 at an output last stage of a video signal. The radio transmitting unit 145 wirelessly transmits the video signal output from an imaging unit 111 to an image processor 102 as a radio signal. The image processor 102 is equipped with a radio receiving unit 146 at an input first-stage of the video signal. The radio receiving unit 146 receives the radio signal transmitted from the endoscope 101, and demodulates the received radio signal into the original video signal. In this way, in the present embodiment, the video signal is transmitted between the endoscope 101 and the image processor 102 using the radio signal.

In the second or third embodiment, as in the present embodiment, the electronic endoscopic apparatus may be configured so that the video signal is transmitted between the endoscope 101 and the image processor 102 using the radio signal.

As described above, according to the present embodiment, the video signal is transmitted using the radio signal. Thereby, it is possible to reduce the number of signal lines required for data transmission, and the endoscope can be made light in weight. Further, an insulating process for securing safety of a testee becomes easy.

(Seventh Embodiment)

Figure 8:
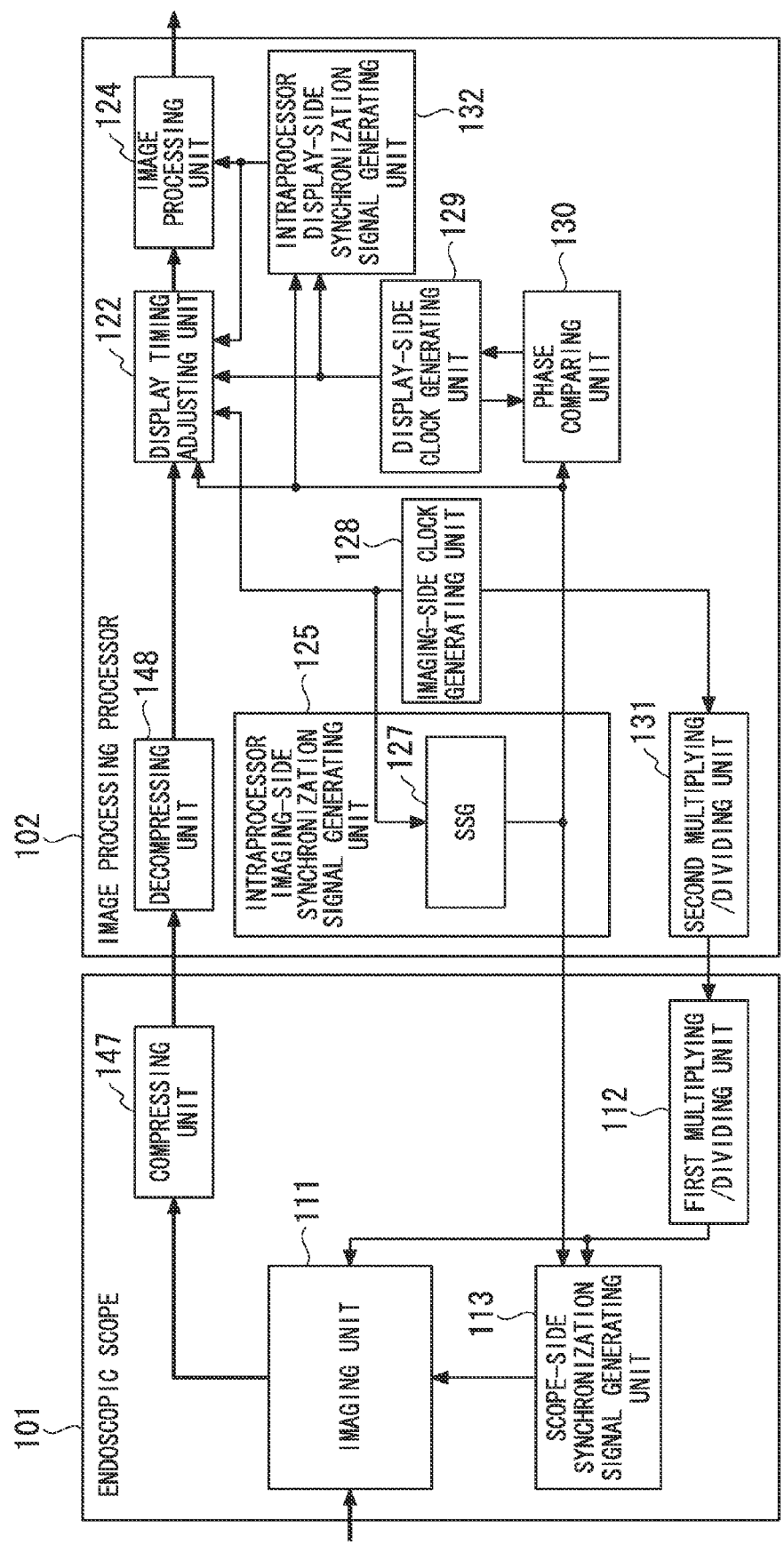
FIG. 8 is a block diagram showing a configuration of an electronic endoscopic apparatus according to a seventh embodiment of the present invention.

Next, a seventh embodiment of the present invention will be described. FIG. 8 shows a configuration of an electronic endoscopic apparatus according to the present embodiment. Hereinafter, portions different from those of the first embodiment will be described.

An endoscope 101 is equipped with a compressing unit 147 at an output last stage of a video signal. The compressing unit 147 compresses the video signal output from an imaging unit 111, and transmits the compressed video signal to an image processor 102 as a compression video signal. The image processor 102 is equipped with an expansion unit 148 at an input first stage of the video signal. The expansion unit 148 receives the compression video signal transmitted from the endoscope 101, and expands the received compression video signal back to the decompressed video signal. In this way, in the present embodiment, the video signal is compressed and transmitted between the endoscope 101 and the image processor 102.

In the second or third embodiment, as in the present embodiment, the electronic endoscopic apparatus may be configured so that the video signal is compressed and transmitted between the endoscope 101 and the image processor 102. Further, in the fourth, fifth, and sixth embodiments, as in the present embodiment, the electronic endoscopic apparatus may also be configured so that the video signal is compressed and transmitted between the endoscope 101 and the image processor 102. In this case, the compressing unit 147 may be disposed just before the electro-optic conversion unit 141, the differential signal generating unit 143, or the radio transmitting unit 145, and the expansion unit 148 may be disposed just behind the photoelectric conversion unit 142, the differential signal demodulating unit 144, or the radio receiving unit 146.

As described above, according to the present embodiment, the compressing and expansion processes are added. Thereby, it is possible to reduce a volume of data, and particularly a stable operation of radio communication can be realized.

(Eighth Embodiment)

Figure 9:
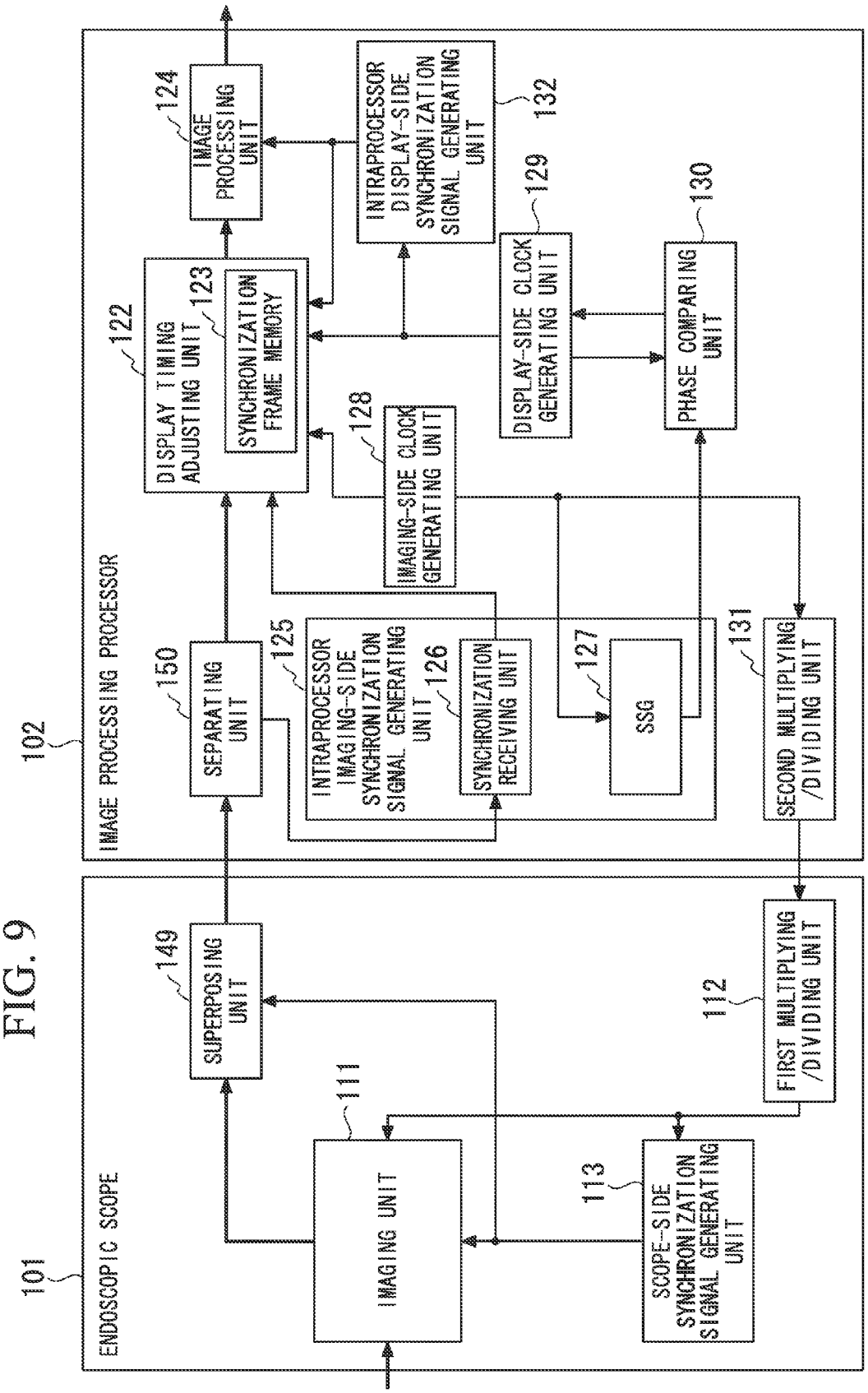
FIG. 9 is a block diagram showing a configuration of an electronic endoscopic apparatus according to an eighth embodiment of the present invention.
Figure 10:
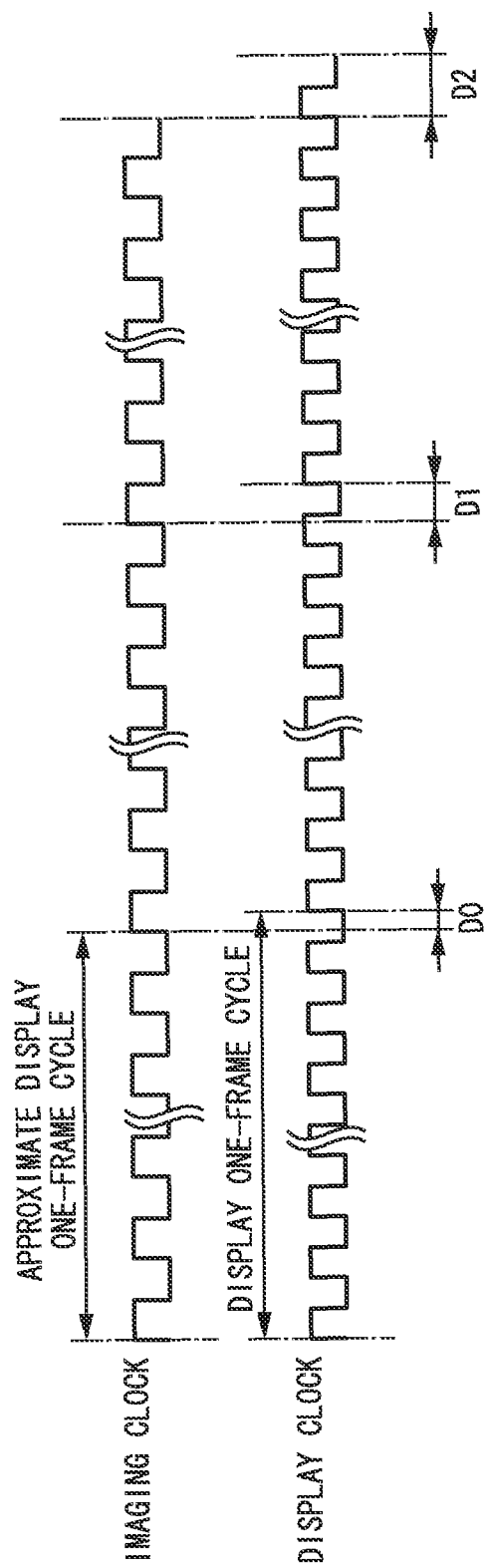
FIG. 10 is a timing chart that explains conventional problems.

Next, an eighth embodiment of the present invention will be described. FIG. 9 shows a configuration of an electronic endoscopic apparatus according to the present embodiment. Hereinafter, portions different from those of the first embodiment will be described.

An endoscope 101 is equipped with a superimposing unit 149 at an output last stage of a video signal. The superimposing unit 149 superimposes a scope-side synchronization signal on the video signal output from an imaging unit 111, and transmits the superimposed signal to an image processor 102 as a compression video signal. The image processor 102 is equipped with a separating unit 150 at an input first stage of the video signal. The separating unit 150 receives the video signal transmitted from the endoscope 101, separates the scope-side synchronization signal from the received video signal, and outputs the separated signal to a synchronization receiving unit 126. In this way, in the present embodiment, the video signal is compressed and transmitted between the endoscope 101 and the image processor 102.

In the third embodiment, as in the present embodiment, the electronic endoscopic apparatus may be configured so that the video signal on which the scope-side synchronization signal is superimposed is transmitted between the endoscope 101 and the image processor 102.

As described above, according to the present embodiment, the scope-side synchronization signal is superimposed on the video signal, and is transmitted to the image processor 102 through the same transmission line. Thereby, the number of transmission lines can be reduced. As such, the endoscope 101 can be reduced in diameter.

While the embodiments of the present invention have been described in detail with reference to the drawings, specific configurations are not limited to these embodiments, and the present invention includes design modifications within a scope not departing from the gist of the present invention is not limited to the above description, but only the attached claims. The present invention is not limited by the above description, but by the appended claims.

What is claimed is:

1. An electronic endoscopic apparatus comprising:
   an endoscope; and
   an image processor, wherein the endoscope includes:
      an imaging unit that converts optical information into an electric signal based on a scope-side clock and a scope-side synchronization signal and output the converted electric signal as a video signal;
      a first multiplying/dividing unit that multiplies and/or divide a transmission clock transmitted from the image processor to generate the scope-side clock; and
      a scope-side synchronization signal generating unit that generates the scope-side synchronization signal,
   the image processor includes:
      an imaging-side clock generating unit that generates an imaging-side clock;
      a second multiplying/dividing unit that multiplies and/or divide the imaging-side clock to generate the transmission clock;
      a display-side clock generating unit that generates a display-side clock;
      an imaging-side synchronization signal generating unit that generates an imaging-side synchronization signal in the image processor;
      a display-side synchronization signal generating unit that generates a display-side synchronization signal in the image processor based on the display-side clock;
      a phase comparing unit that compares a phase of the imaging-side synchronization signal with a phase of the display-side clock and control an oscillation of the display-side clock generating unit based on a result of the comparison; and
      a display timing adjusting unit that receives the video signal output from the endoscope at a timing based on the imaging-side synchronization signal and adjust a synchronization timing of the received video signal to a synchronization timing based on the display-side synchronization signal, and
   a frequency of the display-side clock is M/N times a frequency of the imaging-side clock (M and N are arbitrary natural numbers).

2. The electronic endoscopic apparatus according to claim 1, wherein
   in the endoscope, the scope-side synchronization signal generating unit generates the scope-side synchronization signal synchronized with the imaging-side synchronization signal based on the scope-side clock and the imaging-side synchronization signal; and in the image processor, the imaging-side synchronization signal generating unit spontaneously generates the imaging-side synchronization signal based on the imaging-side clock and transmits the generated signal to the phase comparing unit and the scope-side synchronization signal generating unit.

3. The electronic endoscopic apparatus according to claim 1, wherein in the endoscope, the scope-side synchronization signal generating unit spontaneously generates the scope-side synchronization signal based on the scope-side clock, in the image processor, the imaging-side synchronization signal generating unit includes:

a synchronization signal generating circuit that spontaneously generates a first imaging-side synchronization signal in the image processor based on the imaging-side clock; and a receiving unit that receives the scope-side synchronization signal output from the endoscope and output the received signal as a second imaging-side synchronization signal, the phase comparing unit compares a phase of the first imaging-side synchronization signal and the phase of the display-side clock and controls the oscillation of the display-side clock generating unit based on a result of the comparison, and the display timing adjusting unit has a synchronization frame memory, writes the video signal output from the endoscope to the synchronization frame memory at a timing based on the second imaging-side synchronization signal, and reads out the video signal from the synchronization frame memory at a timing based on the scope-side synchronization signal.

4. The electronic endoscopic apparatus according to claim 1, wherein in the endoscope, the scope-side synchronization signal generating unit spontaneously generates the scope-side synchronization signal based on the scope-side clock, and in the image processor, the imaging-side synchronization signal generating unit has a receiving unit that receives the scope-side synchronization signal output from the endoscope and outputs the received signal as the imaging-side synchronization signal.

5. The electronic endoscopic apparatus according to claim 1, wherein the endoscope includes an electro-optic conversion unit that converts the video signal into an optical signal, and the image processor includes a photoelectric conversion unit that converts the optical signal into the video signal.

6. The electronic endoscopic apparatus according to claim 1, wherein the endoscope includes a conversion unit that converts the video signal into a differential signal, and the image processor includes a demodulating unit that demodulates the differential signal into the video signal.

7. The electronic endoscopic apparatus according to claim 1, wherein the endoscope includes a radio transmitting unit that wirelessly transmits the video signal, and the image processor includes a radio receiving unit that receives the video signal that is wirelessly transmitted by the radio transmitting unit.

8. The electronic endoscopic apparatus according to claim 1, wherein the endoscope includes a compressing unit that compresses the video signal, and the image processor includes an expansion unit that expands the video signal compressed by the compressing unit.

9. The electronic endoscopic apparatus according to claim 3, wherein the endoscope includes a superimposing unit that superimposes the scope-side synchronization signal on the video signal, and the image processor includes a separating unit that separates the scope-side synchronization signal from the video signal on which the scope-side synchronization signal is superimposed by the superimposing unit, and output the separated signal to the receiving unit as the second imaging-side synchronization signal.

10. The electronic endoscopic apparatus according to claim 4, wherein the endoscope includes a superimposing unit that superimposes the scope-side synchronization signal on the video signal, and the image processor includes a separating unit that separates the scope-side synchronization signal from the video signal on which the scope-side synchronization signal is superimposed by the superimposing unit, and output the separated signal to the receiving unit as the imaging-side synchronization signal.

* * * * *